United States Patent
Takagi et al.

(10) Patent No.: US 6,523,416 B2
(45) Date of Patent: Feb. 25, 2003

(54) METHOD FOR SETTING SHAPE AND WORKING STRESS, AND WORKING ENVIRONMENT OF STEEL MEMBER

(75) Inventors: Shusaku Takagi, Chiba (JP); Kaneaki Tsuzaki, Ibaraki (JP); Tadanobu Inoue, Ibaraki (JP)

(73) Assignees: Kawasaki Steel Corporation, Chiba (JP); National Institute For Material Science, Ibaraki (JP)

( * ) Notice: Subject to any disclaimer, the term of this patent is extended or adjusted under 35 U.S.C. 154(b) by 0 days.

(21) Appl. No.: 09/940,669

(22) Filed: Aug. 29, 2001

(65) Prior Publication Data

US 2002/0043111 A1 Apr. 18, 2002

(30) Foreign Application Priority Data

Aug. 31, 2000 (JP) .................................... 2000-264716

(51) Int. Cl.[7] ............................. G01N 3/00; G01N 33/20
(52) U.S. Cl. ...................................... 73/760; 73/19.07
(58) Field of Search .................... 73/760, 56, 763, 73/764, 74, 75, 76, 77, 19.07

(56) References Cited

U.S. PATENT DOCUMENTS

| | | | | |
|---|---|---|---|---|
| 4,475,963 A | * | 10/1984 | Takahashi et al. | 148/503 |
| 4,552,024 A | * | 11/1985 | Baker et al. | 73/821 |
| 6,289,739 B1 | * | 9/2001 | Fujimoto et al. | 73/799 |

FOREIGN PATENT DOCUMENTS

| | | | | |
|---|---|---|---|---|
| JP | 08210958 A | * | 8/1996 | G01N/3/32 |
| JP | 08334445 A | * | 12/1996 | G01N/3/00 |

* cited by examiner

*Primary Examiner*—Benjamin R. Fuller
*Assistant Examiner*—Lilybett Martir
(74) *Attorney, Agent, or Firm*—Young & Thompson

(57) ABSTRACT

A delayed fracture is effectively prevented by appropriately setting a shape and working stress, and working environment of a high strength member having more than 1,000 MPa of tensile strength. For this end, the relationship between a maximum value of diffusible hydrogen contents of unfailed specimens ($H_c$) and Weibull stress are found and the content of diffusible hydrogen entered into steel from the environment due to corrosion during the use of the steel member ($H_e$) is also found. Then, Weibull stress in the $H_c$ that is equal to the $H_e$ is found, thus determining the shape and working stress of the steel member so as to provide stress below the Weibull stress.

5 Claims, 6 Drawing Sheets

METHOD FOR SETTING SHAPE AND WORKING STRESS, AND WORKING ENVIRONMENT OF STEEL MEMBER

BACKGROUND OF THE INVENTION

1. Field of the Invention

The present invention relates to a method to prevent a delayed fracture of a steel member, and relates to a method for setting a shape and working stress, and working environment of a steel member so as to prevent a delayed fracture. More specifically, the present invention relates to a method for setting a shape and working stress, and working environment of a steel member so as to prevent a delayed fracture in steel members using high strength steel or the like having tensile strength of more than 1,000 MPa.

2. Description of the Related Art

Recently, high strength steel having tensile strength of more than 1,000 MPa has been developed. As it is known that a delayed fracture is found from such high strength steel, the steel is rarely employed for practical use. The delayed fracture is a phenomenon where high tensile steel suddenly fractures due to stress at less than tensile strength after a certain period.

Even though the same stress is applied to steel members, some members fracture and others do not due to a difference in stress concentration depending on the shape of the steel members. Thus, steel members have been conventionally designed to prevent stress concentration for the steel members from which a delayed fracture is expected. However, it is practically impossible to completely prevent a delayed fracture simply by changing the shape of steel members. Thus, steel members in complex shapes, such as bolts, have been designed with an extremely high safety factor.

Another method to prevent a delayed fracture is to increase $H_c$, in other words, a maximum value of diffusible hydrogen contents of unfailed specimens. However, a delayed fracture has not yet been prevented completely by the method.

An object of the present invention is to solve the above-noted conventional problems. The purposes of the present invention include: accurate prediction of a delayed fracture of a steel member, complete prevention of a delayed fracture by appropriately setting the shape, working stress and working environment of a steel member, and designing even a steel member in a complex shape with an appropriate safety factor.

SUMMARY OF THE INVENTION

In order to solve the above-noted problems, a method for setting a shape and working stress of a steel member according to the present invention includes the steps of finding the relationship between a maximum value of diffusible hydrogen contents of unfailed specimens ($H_c$) and Weibull stress, and finding the content of diffusible hydrogen entered into steel from the environment due to corrosion during the use of the steel member ($H_e$); finding Weibull stress in the $H_c$ which is equal to the $H_e$; and determining a shape and working stress of the steel member so as to provide stress below the Weibull stress.

It is preferable that the Weibull stress is calculated by an electronic arithmetic unit in accordance with a finite element method based on the following Formula 1:

$$\sigma_w = \left[ \frac{1}{V_0} \int_{V_f} (\sigma_{eff})^m dV_f \right]^{\frac{1}{m}} \quad \text{Formula 1}$$

A method for setting a working environment of a steel member according to the present invention includes the steps of finding the relationship between a maximum value of diffusible hydrogen contents of unfailed specimens ($H_c$) and Weibull stress ($\sigma_w A$), and finding Weibull stress ($\sigma_w B$) of the steel member in actual use based on a shape and working stress of the steel member in actual use; finding $H_c$ in the Weibull stress ($\sigma_w A$) which is equal to the Weibull stress ($\sigma_w B$); and determining a working environment of the steel member so as to provide the content of diffusible hydrogen entered into steel from the environment due to corrosion during the use of the steel member ($H_e$) which is less than the $H_c$.

It is preferable that the Weibull stress ($\sigma_w A$) and the Weibull stress ($\sigma_w B$) are calculated by an electronic arithmetic unit in accordance with a finite element method based on the Formula 1 mentioned above.

A method for evaluating a delayed fracture of a steel member includes the steps of finding the relationship between a maximum value of diffusible hydrogen contents of unfailed specimens ($H_c$) and Weibull stress ($\sigma_w A$), and finding the content of diffusible hydrogen entered into steel from the environment due to corrosion during the use of the steel member ($H_e$); finding the Weibull stress ($\sigma_w A$) in the $H_c$ which is equal to the $H_e$; and comparing the $\rho_w A$ to Weibull stress ($\sigma_w B$) which is calculated from a shape and working stress of the steel member in use, and determining that there will be no delayed fracture when the $\sigma_w A$ is larger than the $\sigma_w B$.

The present invention is based on the following knowledge obtained by the present inventors.

(1) The occurrence of a delayed fracture can be principally predicted based on the Weibull stress ($\sigma_w$) and a maximum value of diffusible hydrogen contents of unfailed specimens ($H_c$). In other words, the occurrence of a delayed fracture can be predicted without depending on a shape and working stress of a steel member.

(2) When a maximum value of diffusible hydrogen contents of unfailed specimens ($H_c$) is larger than the content of diffusible hydrogen entered into steel from the environment due to corrosion during the use of the steel member ($H_e$), a delayed fracture will not occur.

DESCRIPTION OF THE PREFERRED EMBODIMENT

Embodiments of the present invention will be explained. Terms used in the present invention are as follows.

A maximum value of diffusible hydrogen contents of unfailed specimens ($H_c$) means a maximum diffusible hydrogen content in steel when specimens do not fracture under certain load. $H_c$ can be experimentally measured, for instance, by the following method. When voltage is applied to steel samples as a cathode in electrolyte, hydrogen is introduced to the steel. In order to diffuse hydrogen evenly in the samples, the samples may be plated with Cd thereon, and are held or heated at room temperature. Constant load is applied to the samples, and a maximum diffusible hydrogen content is measured for the samples which did not fracture after 100 hours. Diffusible hydrogen contents are measured by the following method. The samples are heated up to 350° C. at a constant gradient between 50° C. and 800° C. per hour, and the content of hydrogen released during the period is measured. Released hydrogen can be quantitatively measured, for instance, by quadrupole mass spectrometer or gas chromatography.

The content of diffusible hydrogen entered into steel from the environment due to corrosion ($H_e$) means a maximum hydrogen content entered into steel from an actual working environment. $H_e$ is empirically and experimentally found from the actual working environment of a steel member. Experimentally, samples are placed into a testing machine where a working environment is reproduced as accurately as possible, and an exposure test is performed. The method of measuring hydrogen contents is the same as the hydrogen content measurement method for the $H_c$.

Figure 2:
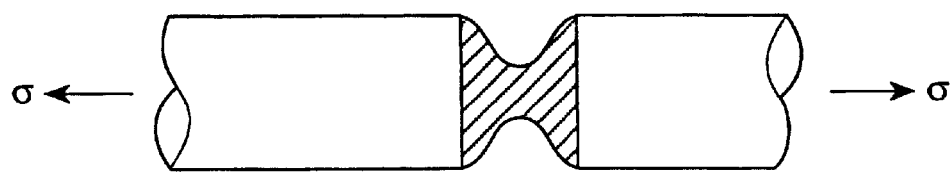
FIG. 2 is a figure, explaining an area $V_f$ that is likely to be fractured.

Weibull stress ($\sigma_w$) is calculated by a mathematical procedure, and can be calculated based on a shape and working stress of a steel member. There are several calculation methods. In the present invention, the Weibull stress ($\sigma_w$) is found by the finite element method of the following Formula 1:

$$\sigma_w = \left[ \frac{1}{V_0} \int_{V_f} (\sigma_{\mathit{eff}})^m \, dV_f \right]^{\frac{1}{m}} \quad \text{Formula 1}$$

wherein $\sigma_{\mathit{eff}}$ is maximum principal stress which influences a fracture; $V_o$ is a reference volume of a certain area where a fracture is likely to occur, and $V_o$ may be any constant and does not influence relative comparison with Weibull stress at any value, and can be, for instance, 1 mm$^3$; $V_f$ indicates an area where a fracture is likely to occur, for instance, a shaded area in relation to stress ($\sigma$) as shown in FIG. 2; and m is a constant called Weibull shape parameter, which is normally 10 to 30. As calculation conditions are determined, Weibull stress can be calculated by using an electronic arithmetic unit based on a finite element method.

Figure 1:
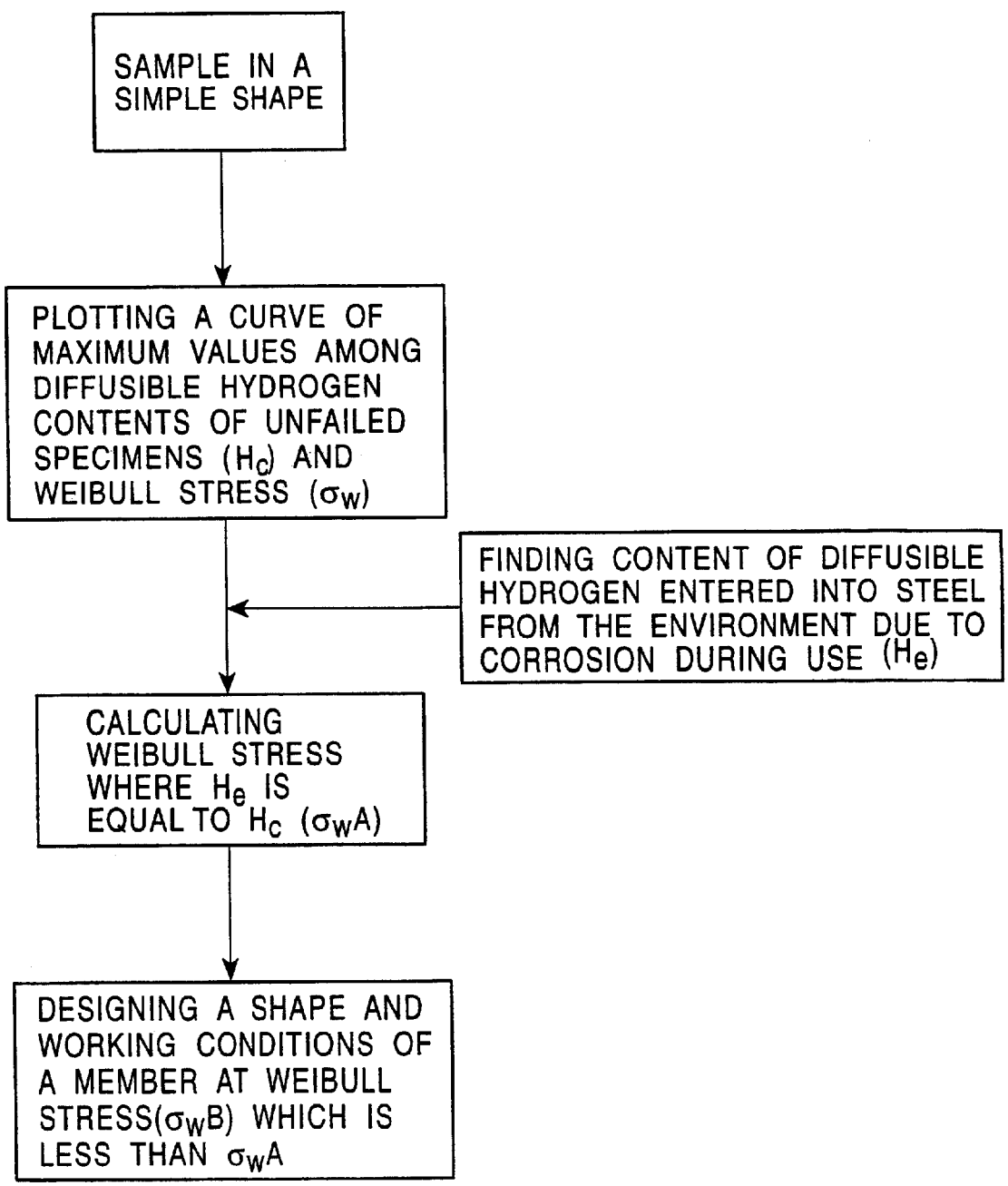
FIG. 1 is a diagram, showing steps of the present invention.
Figure 4:
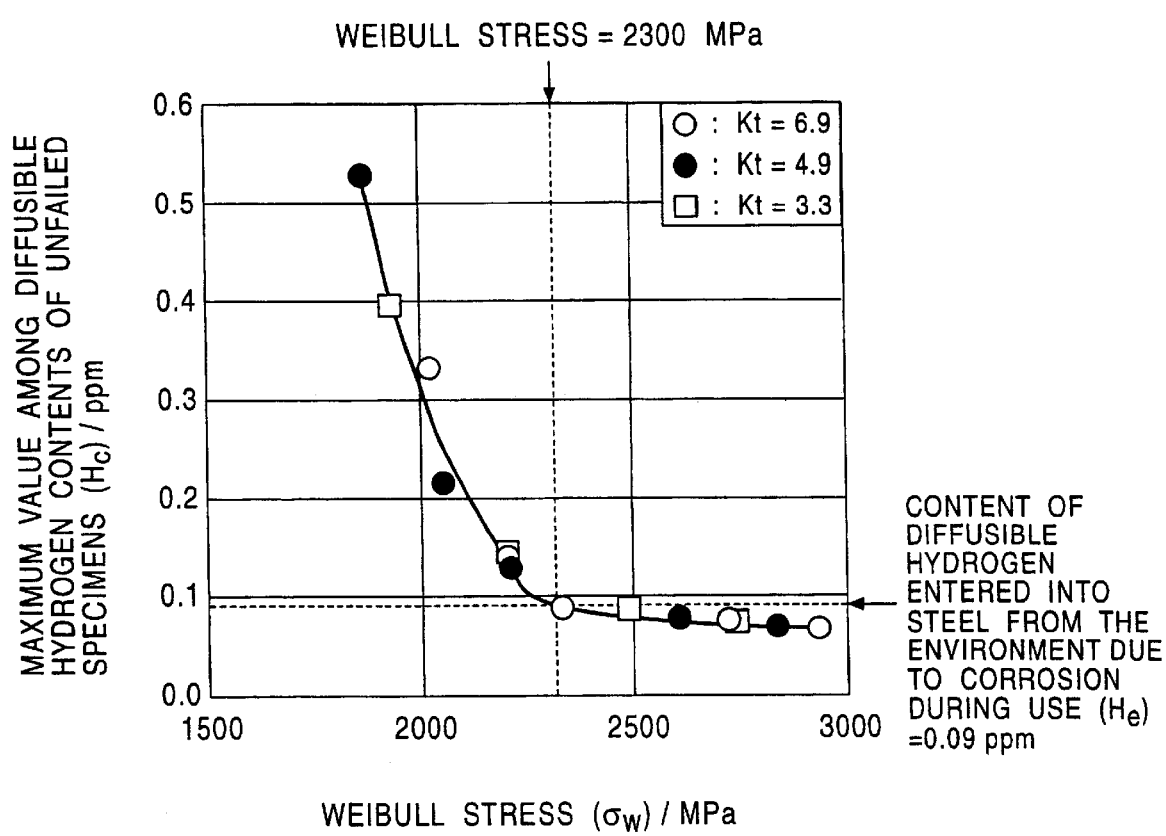
FIG. 4 is a graph, showing the relationship between calculation results of Weibull stress ($\sigma_w$) and measurement results of a maximum value of diffusible hydrogen contents of unfailed specimens ($H_c$)

A typical embodiment of the present invention will be explained in detail. FIG. 1 is a diagram, showing the steps of the present invention. First, a maximum value of diffusible hydrogen contents of unfailed specimens ($H_c$) is measured, and Weibull stress is then calculated from samples in a simple shape. Relationships between $H_c$ and the Weibull stress are found, and a plotted curve of maximum values of diffusible hydrogen contents of unfailed specimens ($H_c$) and the Weibull stress ($\sigma_w$) is prepared. FIG. 4 is a typical example of this curve. On the other hand, the content of diffusible hydrogen entered into a steel member in use from the environment due to corrosion ($H_e$) is experimentally measured or predicted from empirical values. Subsequently, Weibull stress ($\sigma_w$A) in $H_c$ which is equal to $H_e$, is calculated from the curve. A shape and working stress of a steel member in actual use are determined so as to provide Weibull stress ($\sigma_w$B) which is less than the Weibull stress ($\sigma_w$A). In other words, the shape and working stress of a steel member in actual use are determined so as to provide $\sigma_w$A>$\sigma_w$B. When $\sigma_w$A>$\sigma_w$B, no delayed fracture is found in the steel member. When $\sigma_w$A$\leq$$\sigma_w$B, a delayed fracture is likely to be found in the steel member. In this case, the shape and working stress of the steel member in actual use are corrected, and the Weibull stress ($\sigma_w$B) is calculated again. The above-noted correction is repeated until $\sigma_w$A>$\sigma_w$B. In this way, the shape and working stress of the steel member in actual use can be appropriately designed.

The present invention determines a working environment of a steel member so as to provide the content of diffusible hydrogen entered into steel from the environment due to corrosion during the use of the steel member ($H_e$), which is smaller than the maximum value of diffusible hydrogen contents of unfailed specimens ($H_c$) in the Weibull stress ($\sigma_w$B) calculated on the basis of the shape and working stress of the steel member in actual use. In other words, the working environment of the steel member in actual use is determined so as to provide $H_c$>$H_e$. The working environment indicates, for instance, temperature, humidity, components of atmospheric gas, floating salt in the atmosphere and the like in a place where a steel member is used. Specifically, it means an environment where a steel member is used, such as the seaside, inside an engine room of a vehicle, inside a tunnel on a freeway, and the like.

The present invention finds relationships between a maximum value of diffusible hydrogen contents of unfailed specimens ($H_c$) and Weibull stress ($\sigma_w$A), and finds the content of diffusible hydrogen entered into steel from the environment due to corrosion during the use of the steel member ($H_e$) Subsequently, the Weibull stress ($\sigma_w$A) is found in the $H_c$ which is equal to the $H_e$, and the Weibull stress ($\sigma_w$A) is compared to Weibull stress ($\sigma_w$B) which is calculated from a shape and working stress of the steel member in use. It is determined that there will be no delayed fracture when $\sigma_w$A is larger than $\sigma_w$B. According to the present invention, the occurrence of a delayed fracture can be accurately predicted for a steel member.

According to the present invention, even if a steel member in actual use has a complex shape, it could be designed with an appropriate safety factor. It becomes practically easy to use high strength steel which has tensile strength of more than 1,000 MPa and has been hardly used in a practical way. Various types of devices, machines and the like can be reduced in weight, thus improving the energy efficiency of society as a whole.

Moreover, the present invention is applicable to every steel member as a component without depending on the composition of the steel member. The present invention is preferably applied to high strength steel which has tensile strength of more than 1,000 MPa and has been rarely employed for practical use.

EXAMPLES

Figure 3:
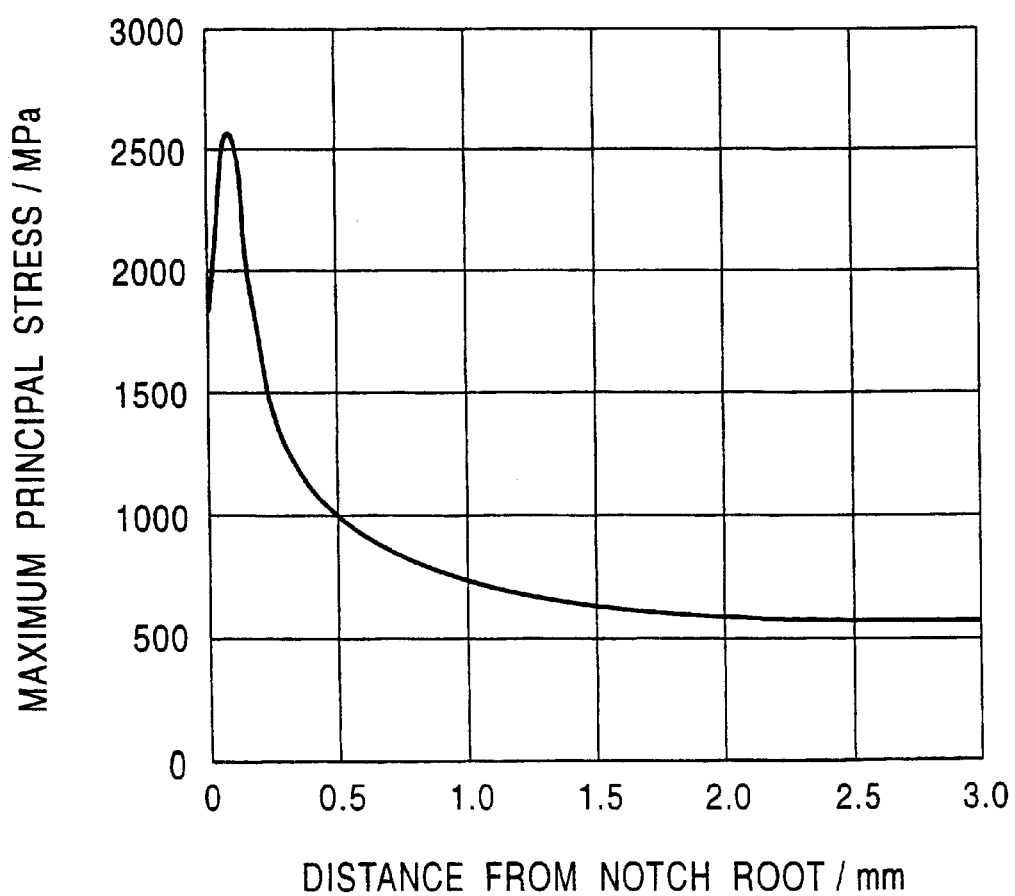
FIG. 3 is a graph, showing the relationship between distances from a notch root and maximum principal stress.

Table 1 shows conditions of a delayed fracture test. Symbols in Table 1 will be explained. $K_t$ indicates a stress concentration factor, and is a constant which is determined by a notch shape of a sample. For instance, a sample having no notch has $K_t$ of 1.0. $\sigma_w$ is calculated Weibull stress. $\sigma_{max}$ is maximum applied stress. $\sigma_{ave}$ is average applied stress. $H_c$ is a measured maximum value of diffusible hydrogen contents of unfailed specimens. A used steel member has tensile strength of about 1,400 MPa. The chemical components thereof are 0.40% of C, 0.24% of Si, 0.8% of Mn, 0.02% of P, 0.007% of S, 1.0% of Cr and 0.16% of Mo in mass %. The remnant consists of Fe and inevitable impurities. The sample is a round bar having a diameter of 10 mm, and has a ring notch at the center. $H_c$ was measured under each condition. The Weibull stress ($\sigma_w$) under each condition was calculated based on the finite element method (implicit solution method) by using commercial analyzing software. $V_o=1$ mm$^3$ and m=20 when the Weibull stress ($\sigma_w$) was calculated. Since it was found that $\sigma_w$ and $H_c$ have principal relations and are not influenced by $K_t$ only in case of m=20. Typical maximum applied stress ($\sigma_{max}$) for calculation is shown in FIG. 3. FIG. 3 shows the relationship between distances from a notch root of a sample and maximum principal stress ($\sigma_{max}$). In this example, $K_t=4.9$ and applied stress/tensile strength of notched specimens=0.47 in accordance with Table 1. As shown in FIG. 3, the maximum applied stress ($\sigma_{max}$) changes in a tensile direction. The stress is at the maximum of 2,544 MPa near a notch root, and sharply decreases as it is apart from the notch root. The stress becomes constant at 587 MPa at a location fully apart from the notch root. The stress is not at the maximum level at the notch root because the material has a partial yield and plastic deformation in this example. FIG. 2 shows an area $V_f$ which is used for the calculation of the Weibull stress ($\sigma_w$). $V_f$ is an area which is likely to be fractured.

FIG. 4 shows the relationship between calculation results of the Weibull stress ($\sigma_w$) and measurement results of maximum values of diffusible hydrogen contents of unfailed specimens ($H_c$) It is found from FIG. 4 that $\sigma_w$ and $H_c$ have principal relations and are not influenced by $K_t$. This knowledge is extremely useful in predicting the occurrence of a delayed fracture. The content of diffusible hydrogen entered into steel from the environment due to corrosion ($H_e$) of the steel member can be empirically predicted from the working environment. It is found that the $H_e$ of the steel member is 0.05 to 0.09 ppm. According to FIG. 4, $\sigma_w$ is 2,300 MPa when $H_e$ is 0.09 ppm. Accordingly, it is possible to predict that the occurrence of a delayed fracture of the steel member is zero at less than 2,300 MPa of $\sigma_w$.

Figure 5:
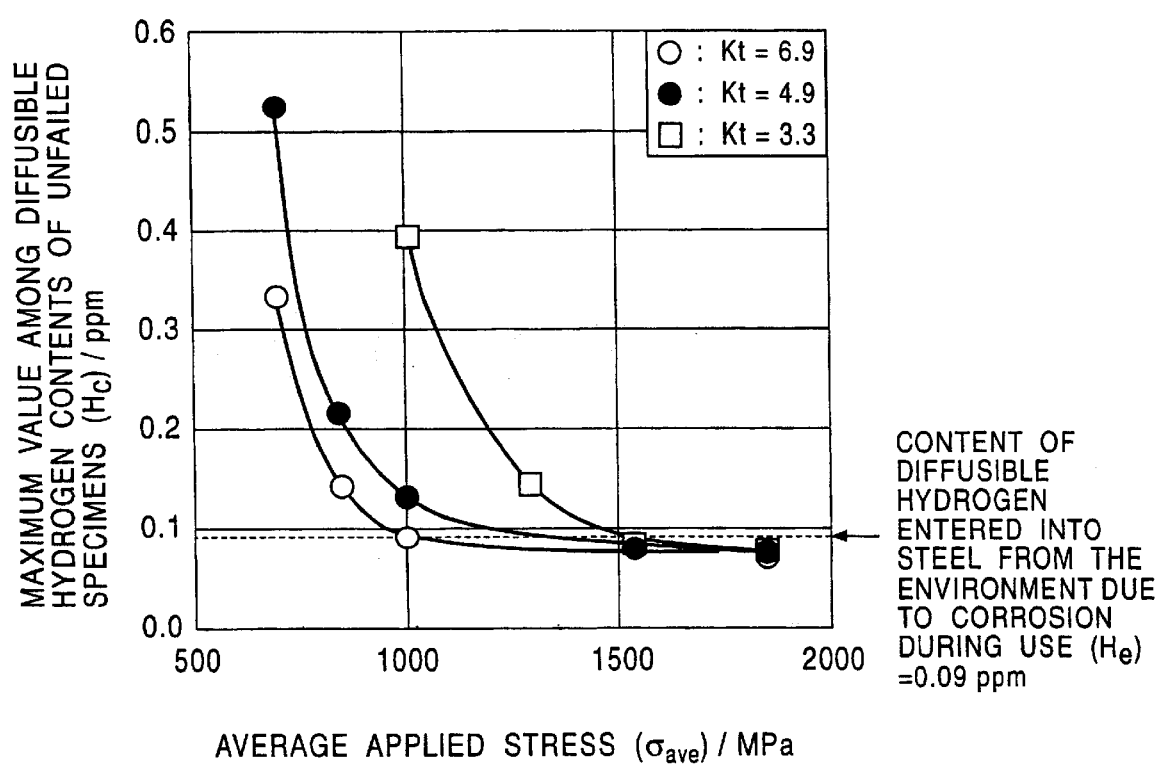
FIG. 5 is a graph, showing the relationship between calculation results of average applied stress ($\sigma_{ave}$) and measurement results of a maximum value of diffusible hydrogen contents of unfailed specimens ($H_c$)

FIG. 5 shows the relationship between calculation results of average applied stress ($\sigma_{ave}$) and measurement results of maximum values of diffusible hydrogen contents of unfailed specimens ($H_c$) It is found, from FIG. 5, that $\sigma_{ave}$ and $H_c$ have no principal relations and are heavily influenced by $K_t$. It is known that the steel member has 0.05 to 0.09 ppm of $H_e$. However, it is almost impossible to predict, from FIG. 5, the level of the average applied stress ($\sigma_{ave}$) from which the steel member will have no delayed fracture. This is because $\sigma_{ave}$ where $H_c$ is larger than $H_e$ becomes different when $K_t$ is different.

From FIG. 4, the occurrence of a delayed fracture of the steel member is predicted to be zero when $\sigma_w$ is less than 2,300 MPa. A test was carried out to confirm whether or not this prediction was correct. An exposure test was performed under the same stress conditions as for the delayed fracture test. For the test, predetermined load was applied on samples. Three-percent salt solution was sprayed on the samples twice, in the morning and in the evening, and the samples were examined for fracture after 100 hours. The occurrence of a delayed fracture is found by performing the exposure test to twenty samples under each condition, and is a value where the number of fractured samples is divided by 20.

Figure 6:
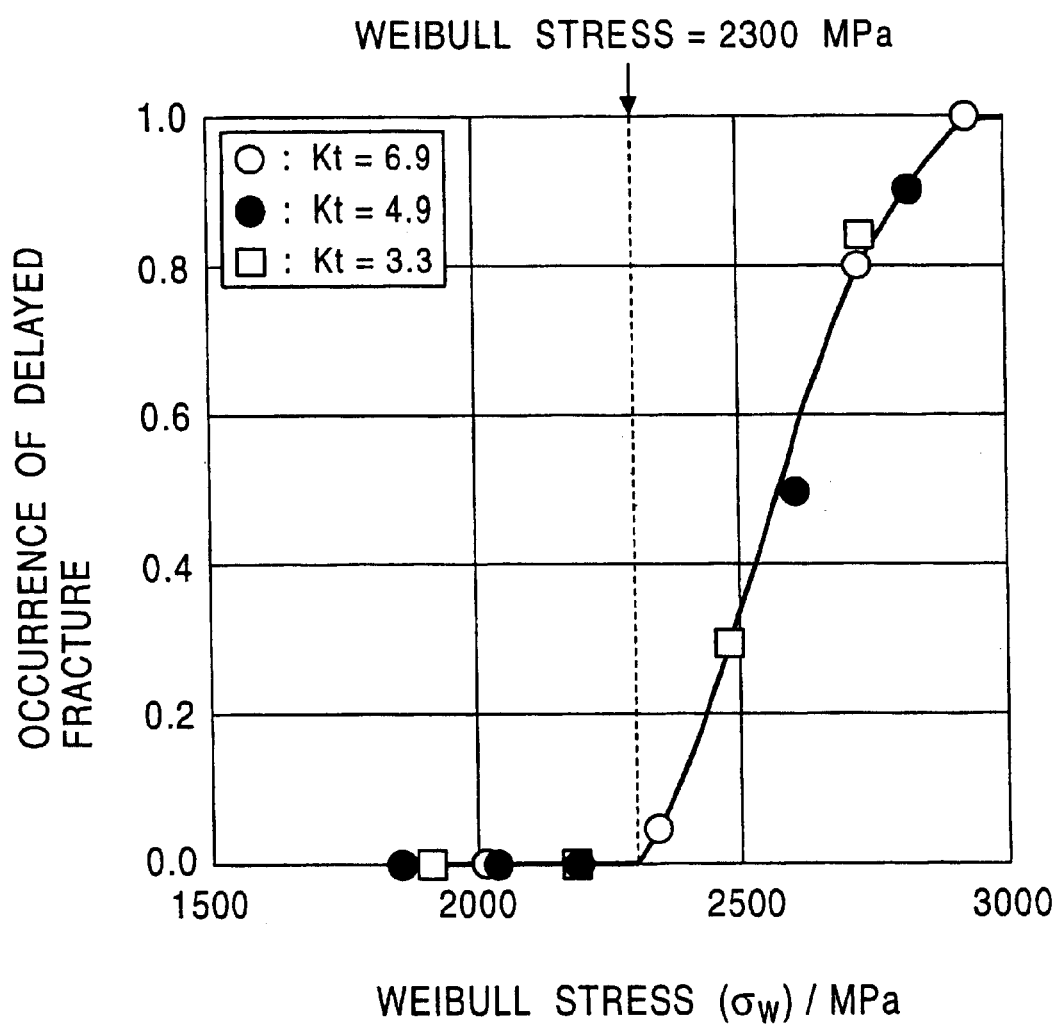
FIG. 6 is a graph, showing effects of Weibull stress ($\sigma_w$) on the occurrence of a delayed fracture.

FIG. 6 shows the results of the exposure test. FIG. 6 shows the effects of $\sigma_w$ on the occurrence of a delayed fracture. When $\sigma_w$ was less than 2,300 MPa, the occurrence of a delayed fracture was zero. At 2,300 MPa or higher, the occurrence of a delayed fracture went up as $\sigma_w$ increased. Accordingly, it is realized that the prediction based on FIG. 4 was correct, that is the occurrence of a delayed fracture of the steel member is zero at less than 2,300 MPa of $\sigma_w$. In other words, even if a steel member has a different shape from that of the steel member used for the delayed fracture test, a delayed fracture can be prevented as the steel member is designed at less than 2,300 MPa of $\sigma_w$.

Figure 7:
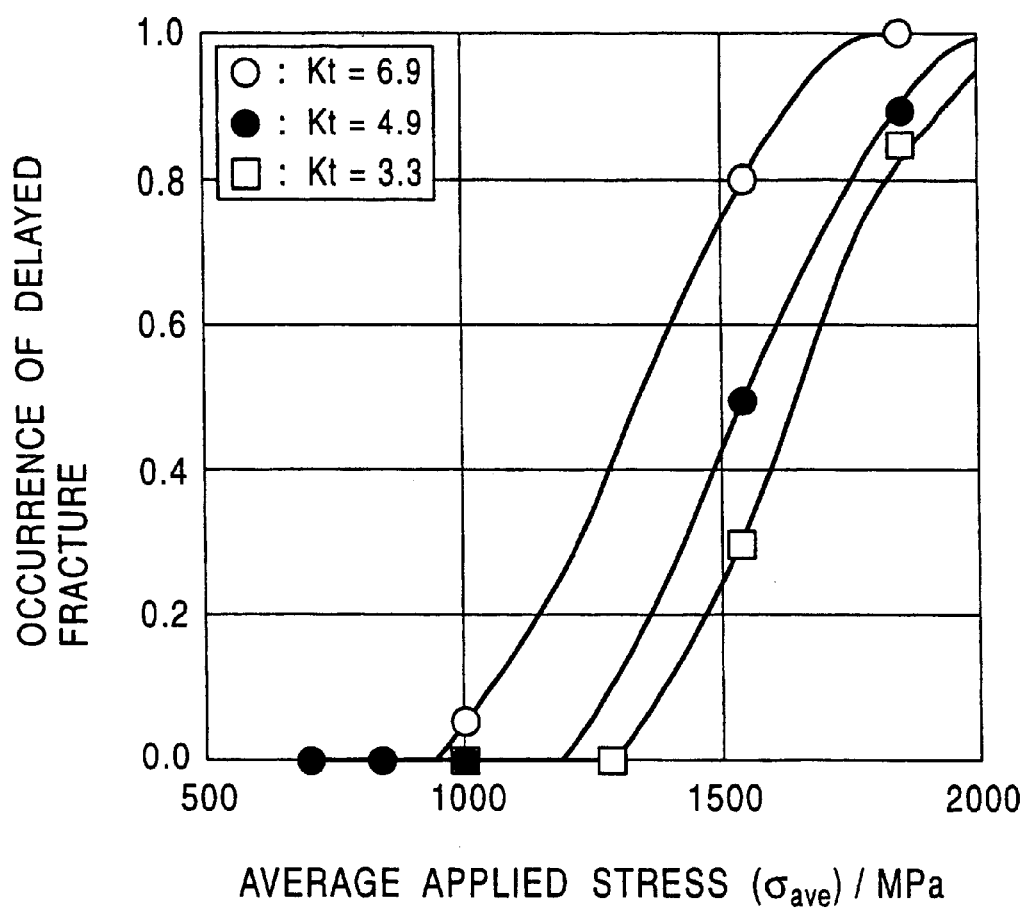
FIG. 7 is a graph, showing effects of average applied stress ($\sigma_{ave}$) on the occurrence of a delayed fracture.

FIG. 7 shows the effects of $\sigma_{ave}$ on the occurrence of a delayed fracture. FIG. 7 has been conventionally used for the prediction of a delayed fracture. When the stress concentration factor ($K_t$) is different, a critical $\sigma_{ave}$ that provides zero occurrence of a delayed fracture, becomes different. It is almost impossible to predict the level of $\sigma_{ave}$ from which no delayed fracture is caused in the steel member. It is also difficult to predict the occurrence of a delayed fracture of a steel member having a different shape from that of the steel member to which the delayed fracture test was carried out. It is obvious that, in the conventional method, a delayed fracture test has to be carried out to every design shape of a steel member.

The present invention can accurately predict whether or not a steel member will have a delayed fracture. The present invention can also effectively prevent a delayed fracture by appropriately setting the shape and working stress, and working environment of a steel member. Even a steel member having a complex shape can be designed with an appropriate safety factor for actual use. The practical use of high strength steel having more than 1,000 MPa of tensile strength and previously hardly used, becomes easy. Various types of devices, machines and so forth can thus be reduced in weights, improving energy efficiency of society as a whole.

TABLE 1

| | | | Conditions of Delayed Fracture Test | | | | |
|---|---|---|---|---|---|---|---|
| Sample diameter/mm | Kt | Applied stress/tensile strength of notched specimen | σw/MPa | σmax/MPa | σave/MPa | Hc/mass ppm | Occurrence of delayed fracture |
| 10 | 6.9 | 0.86 | 2930 | 3434 | 1849 | 0.0692 | 1.00 |
| 10 | 6.9 | 0.72 | 2715 | 3274 | 1543 | 0.0794 | 0.80 |
| 10 | 6.9 | 0.47 | 2334 | 2860 | 1004 | 0.0908 | 0.10 |

TABLE 1-continued

Conditions of Delayed Fracture Test

| Sample diameter/mm | Kt | Applied stress/tensile strength of notched specimen | σw/MPa | σmax/MPa | σave/MPa | Hc/mass ppm | Occurrence of delayed fracture |
|---|---|---|---|---|---|---|---|
| 10 | 6.9 | 0.40 | 2196 | 2710 | 841 | 0.1408 | 0.00 |
| 10 | 6.9 | 0.33 | 2021 | 2494 | 701 | 0.3355 | 0.00 |
| 10 | 4.9 | 0.86 | 2828 | 3164 | 1849 | 0.0729 | 0.90 |
| 10 | 4.9 | 0.72 | 2606 | 2961 | 1543 | 0.0812 | 0.50 |
| 10 | 4.9 | 0.47 | 2203 | 2544 | 1004 | 0.1276 | 0.00 |
| 10 | 4.9 | 0.40 | 2047 | 2379 | 841 | 0.2151 | 0.00 |
| 10 | 4.9 | 0.33 | 1863 | 2187 | 701 | 0.5240 | 0.00 |
| 10 | 3.3 | 0.86 | 2732 | 2808 | 1849 | 0.0754 | 0.85 |
| 10 | 3.3 | 0.72 | 2478 | 2590 | 1543 | 0.0850 | 0.30 |
| 10 | 3.3 | 0.60 | 2194 | 2364 | 1291 | 0.1439 | 0.00 |
| 10 | 3.3 | 0.47 | 1921 | 2110 | 1004 | 0.3940 | 0.00 |

What is claimed is:

1. A method for setting a shape and working stress of a steel member comprising the steps of:

determining the relationship between a maximum content $H_c$ among diffusible hydrogen contents of unfailed steel specimens and Weibull stress;

measuring an environment content $H_e$ of diffusible hydrogen penetrating the steel member from the environment;

determining the Weibull stress $\sigma_w A$ when $H_c = H_e$; and determining the shape and working stress of the steel member when the Weibull stress $\sigma_w B$ in actual use is below the Weibull stress $\sigma_w A$.

2. The method according to claim 1, wherein the Weibull stress is calculated by an electronic arithmetic unit in accordance with a finite element method based on the following Formula 1:

$$\sigma_w = \left[\frac{1}{V_0}\int_{V_f}(\sigma_{\text{eff}})^m dV_f\right]^{\frac{1}{m}} \quad \text{Formula 1}$$

wherein $\sigma_{\text{eff}}$ is maximum principal stress which influences a fracture; $V_o$ is a reference volume of a certain area where a fracture is likely to occur; $V_f$ is an area where a fracture is likely to occur; and m is a constant called Weibull shape parameter.

3. A method for setting a working environment of a steel member comprising the steps of:

determining the relationship between a maximum content $H_c$ among diffusible hydrogen contents of unfailed steel specimens and Weibull stress $\sigma_w A$;

determining Weibull stress $\sigma_w B$ of the steel member in actual use based on a shape and working stress of the steel member in actual use;

determining $H_c$ when $\sigma_w A = \sigma_w B$; and determining a working environment of the steel member when a content of diffusible hydrogen penetrating the steel member from the environment $H_e$ is below the $H_c$.

4. The method according to claim 3, wherein the Weibull stress is calculated by an electronic arithmetic unit in accordance with a finite element method based on the following Formula 1:

$$\sigma_w = \left[\frac{1}{V_0}\int_{V_f}(\sigma_{\text{eff}})^m dV_f\right]^{\frac{1}{m}} \quad \text{Formula 1}$$

wherein $\sigma_{\text{eff}}$ is maximum principal stress which influences a fracture; $V_o$ is a reference volume of a certain area where a fracture is likely to occur; $V_f$ is an area where a fracture is likely to occur; and m is a constant called Weibull shape parameter.

5. A method for setting a shape and working stress of a steel member comprising the steps of:

determining the relationship between a maximum content $H_c$ among diffusible hydrogen contents of unfailed steel specimens and Weibull stress $\sigma_w A$;

measuring an environment content $H_e$ of diffusible hydrogen penetrating the steel member from the environment;

determining the Weibull stress $\sigma_w A$ when $H_c = H_e$; and comparing the $\sigma_w A$ to the Weibull stress $\sigma_w B$ which is calculated from a shape and working stress of the steel member in use, and determining that there will be no delayed fracture when the $\sigma_w A$ is larger than the $\sigma_w B$.

* * * * *